(12) United States Patent
Peters

(10) Patent No.: US 7,423,152 B2
(45) Date of Patent: Sep. 9, 2008

(54) PROCESS FOR THE MANUFACTURE OF INTERMEDIATES IN CAMPTOTHECIN PRODUCTION

(75) Inventor: Rene Peters, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 301 days.

(21) Appl. No.: 11/357,273

(22) Filed: Feb. 17, 2006

(65) Prior Publication Data

US 2006/0189807 A1    Aug. 24, 2006

(30) Foreign Application Priority Data

Feb. 22, 2005    (EP) .................................. 05101338

(51) Int. Cl.
*C07D 471/02*    (2006.01)
*C07D 491/02*    (2006.01)
*C07D 498/02*    (2006.01)
(52) U.S. Cl. .................................................... 546/116
(58) Field of Classification Search ................... 546/116
See application file for complete search history.

(56) References Cited

U.S. PATENT DOCUMENTS 6,063,923 A * 5/2000 Fang et al. .................. 544/361

OTHER PUBLICATIONS

Wall et al., Am. Chem. Soc., 3, pp. 327 (1993).
Thomas et al., Bioorg. Med. Chem., 12, pp. 1585-1604 (2004).
Ciufolini et al., Targets in Hetercyclic Systems, 4, pp. 25-55 (2000).
Ciufolini et al., Tetrahedron, 53, pp. 11049-11060 (1997).
Comins et al., J. Am. Chem. Soc., 114, pp. 10971-10972 (1992).
Tan et al., Tetrahedron, 58, pp. 7403-7410 (2002).
Comins et al., J. Org. Chem., 59, pp. 5120-5121 (1994).
Comins et al., Tetrahedron Lett., 35, pp. 5331-5334 (1994).
Peters, et al., Org. Biomol. Chem., 4, pp. 498-509 (2006).

* cited by examiner

*Primary Examiner*—D. Margaret Seeman
*Assistant Examiner*—Niloofar Rahmani
(74) *Attorney, Agent, or Firm*—George W. Johnston; Patricia S. Rocha-Tramaloni; Gene J. Yao

(57) ABSTRACT

The present invention provides a process for the manufacture of the compound of formula (1):

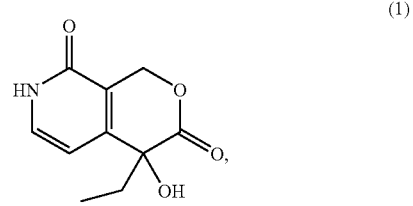

which is a key intermediate in the manufacture of camptothecin (CPT). This compound continues to serve as an attractive and promising lead structure for the development of new anti-cancer drugs.

12 Claims, No Drawings

PROCESS FOR THE MANUFACTURE OF INTERMEDIATES IN CAMPTOTHECIN PRODUCTION

PRIORITY TO RELATED APPLICATIONS

This application claims the benefit of European Application No. 05101338.1, filed Feb. 22, 2005, which is hereby incorporated by reference in its entirety.

FIELD OF THE INVENTION

The present invention relates to a new process for the manufacture of the bicyclic "DE-Fragment," a key intermediate in the manufacture of camptothecin and derivatives thereof.

BACKGROUND OF THE INVENTION

The alkaloid camptothecin (CPT, 3), which has been isolated in 1958 by Wani and Wall from the Chinese tree *Camptotheca accuminata*, shows potent antiproliferative activity (M. E. Wall in *Chronicles of Drug Discovery*, D. Lednicer (Ed.), Am. Chem. Soc.: Washington D.C., 1993; Vol. 3, p. 327). The structure of the pentacyclic skeleton, which was also determined by Wani and Wall eight years after its discovery, contains a highly electrophilic α-hydroxy-δ-lactone ring (ring E, scheme 1), which contains the only stereocenter in form of a tertiary alcohol.

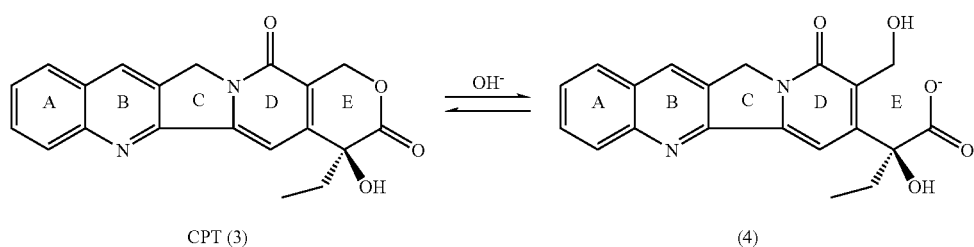

Scheme 1

CPT (3)      (4)

Despite its shortcomings, due to rapid hydrolysis in basic and neutral media towards the open chain carboxylate form (4, scheme 1), CPT continues to serve as an attractive and promising lead structure for the development of new anticancer drugs (see for example C. J. Thomas, N. J. Rahier, S. M. Hecht, *Bioorg. Med. Chem.* 2004, 12, 15851604).

Despite numerous attempts to develop a practical synthesis of camptothecin and derivatives thereof, up to now no really efficient synthesis is available. This is mainly because the currently known synthetic approaches suffer either from very low yields, expensive or commercially not available reagents or highly toxic reagents which may cause health hazard and environmental problems. Another major drawback of most current synthesis routes is an extensive need for column chromatographies during the reaction sequence.

SUMMARY OF THE PRESENT INVENTION

The present invention addresses this problem by providing a novel synthesis route for the bicyclic "DE-Fragment" (s. scheme 1 for nomenclature), a key intermediate in the manufacture of CPT and derivatives thereof. The synthesis according to the present invention is based on simple, easily available and harmless starting materials and reagents, and uses straightforward carbonyl chemistry. Furthermore, the synthesis according to the present invention avoids laborious chromatography and therefore provides improved yields of the desired product.

In particular, the present invention provides a process for the manufacture of the compound of formula (1):

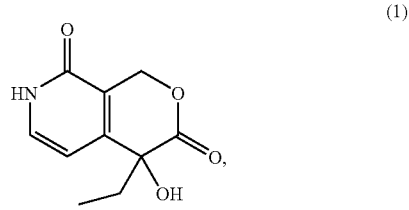

comprising:

a) reacting a compound of formula (I):

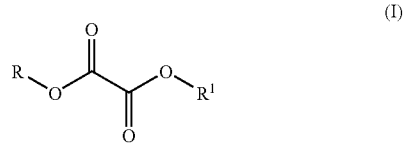

with an amine of formula $HNR^2R^3$ to obtain a compound of formula (II):

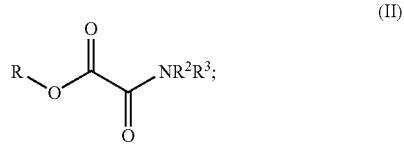

b) further reacting the compound of formula (II) with an ethyl-base to obtain a compound of formula (III):

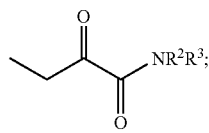

c) further reacting the compound of formula (III) with a compound of formula (IV):

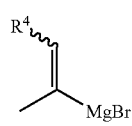

to obtain a compound of formula (V):

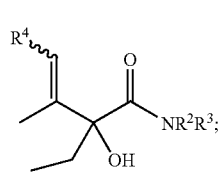

d) further reacting the compound of formula (V) with ozone to obtain a compound of formula (VI):

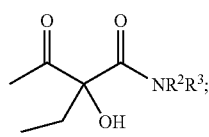

e) further reacting the compound of formula (VI) with a compound of formula (VII):

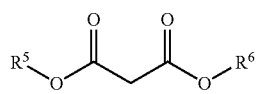

and a base, to obtain the compound of formula (VIII):

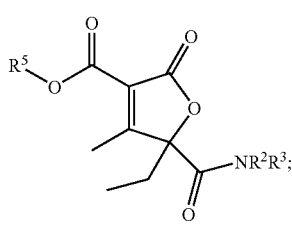

f) further reacting the compound of formula (VIII) with di($C_1$-$C_6$)-alkylformamide di($C_1$-$C_6$)-alkylacetal or a compound of the formula $(R^7R^8N)_3$—CH to obtain a compound of formula (IX):

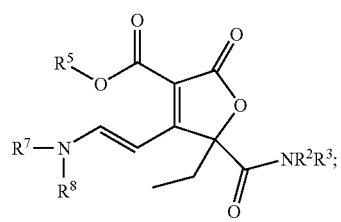

g) further reacting the compound of formula (IX) with ammonium acetate to obtain a compound of formula (X):

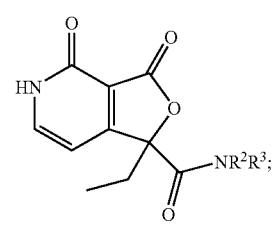

h) further reacting the compound of formula (X) in the presence of alkali metal borohydrides and earth metal salts to give a compound of formula (XI):

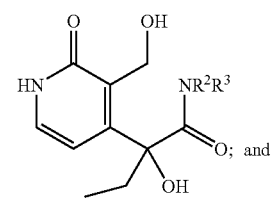

i) further reacting the compound of formula (XI) with concentrated mineral acids to obtain the compound of formula (1);

wherein:
R, $R^1$, $R^7$ and $R^8$ independently from each other are ($C_1$-$C_6$)-alkyl;
$R^2$, $R^3$ and $R^4$ independently from each other are selected from the group consisting of ($C_1$-$C_6$)-alkyl and ($C_3$-$C_7$)-cycloalkyl; and
$R^5$ and $R^6$ independently from each other are selected from the group consisting of ($C_1$-$C_6$)-alkyl and an aryl group.

DETAILED DESCRIPTION

The term "($C_1$-$C_6$)-alkyl" as used herein means a straight chain or branched hydrocarbon, having from one to six, preferably from one to four carbon atoms, such as methyl, ethyl, propyl, isopropyl, butyl, 2-butyl, tert-butyl and the like.

The term "($C_3$-$C_{12}$)-alkyl" as used herein means a straight chain, branched, mono-, di- or tri-cyclic saturated hydrocarbon, having from three to twelve, preferably from three to ten carbon atoms. Preferably said "(C$_3$-C$_{12}$)-alkyl" is attached via a tertiary carbon atom. Preferred examples are tert-butyl or adamantyl.

The term (C$_3$-C$_7$)-cycloalkyl as used herein means a monocyclic, saturated hydrocarbon, having from three to seven, preferably five or six carbon atoms, such as cyclopropyl, cyclopentyl, cyclohexyl, cycloheptyl and the like.

The term "aryl" as used herein means a mono-, bi- or tricyclic, aromatic hydrocarbon, having from six to fourteen, preferably from six to ten, carbon atoms such as phenyl, biphenyl, naphthyl or antracenyl.

The term "ethyl-base" as used herein refers to basic organometal compounds, such as for example Grignard-reagents (Et MgHal), wherein "Hal" means halide. Preferable examples include Et MgBr or ethyl-alkali-metal compounds such as EtLi, or mixed organometal compounds such as Et$_3$AlLi or Et$_3$ZnLi.

The "base," as mentioned under reaction step e) above is preferably an alkali-metal carbonate or -hydride, such as Na$_2$CO$_3$, K$_2$CO$_3$ or Cs$_2$CO$_3$; or NaH or KH. The use of Cs$_2$CO$_3$ is especially preferred.

The term "alkali metal borohydrides" as used in reaction step h) above, is preferably LiBH$_4$ or NaBH$_4$. The use of NaBH$_4$ is especially preferred.

The term "earth metal salts" as used in reaction step h) above, means preferably conventional salts of rare earth metals, preferably halides such as chlorides and bromides; or triflates. Especially preferred is the use of EuCl$_3$ or CeCl$_3$.

The term "mineral acids" as used under reaction step i) above is well known to the skilled artisan and represents inorganic acids, such as HCl, HBr, HNO$_3$, H$_2$SO$_4$ and the like. According to the present invention the use of HCl is especially preferred.

The symbol $$R^4 \quad \text{or} \quad R^{4'}$$

means that the group R$^4$ or R$^{4'}$, when attached to a double bond, may be present in (Z)- or (E)-configuration.

The term "alkali metal- or earth alkali metal hydroxide" [as mentioned herein under reaction step cc)] means LiOH, NaOH, KOH, Ca(OH)$_2$ or Ba(OH)$_2$. The use of LiOH is especially preferred.

The term "tertiary amine" as used herein under reaction step dd) is well known to the skilled artisan and means a basic amine, preferably a trialkyl amine. Examples of such tertiary amines are ethyl di-isoproylamine, triethyl amine and the like.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

A preferred embodiment of the present invention is the process as described above, for the manufacture of the compound of formula (1a):

(1a)

comprising:
aa) reacting the compound of formula (2):

(2)

with a chiral secondary alcohol of the formula R$^9$OH to obtain an ester of formula (IIIa):

(IIIa)

bb) further reacting the ester of formula (IIIa) with a compound of formula (IVa):

(IVa)

to obtain a compound of formula (Va):

(Va)

cc) chemically cleaving the ester from the compound of formula (Va) in the presence of an alkali metal- or earth alkali metal hydroxide and optionally in the presence of hydrogen peroxide, to obtain the compound of formula (Vb):

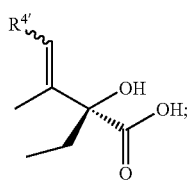

(Vb)

dd) further reacting the compound of formula (Vb) with a tertiary amine and thionyl chloride, then subsequently adding an amine of formula $HNR^{2'}R^{3'}$ to obtain a compound of formula (Vc):

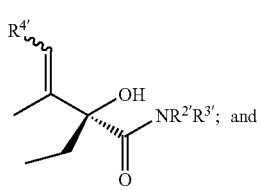

(Vc)

then performing the reaction steps d) to i) as described previously to obtain the compound of formula (1a);

wherein:

$R^{2'}$, $R^{3'}$ and $R^{4'}$ independently from each other are selected from the group consisting of $(C_1\text{-}C_6)$-alkyl and $(C_3\text{-}C_7)$-cycloalkyl;

—$OR^9$ is selected from the group consisting of:

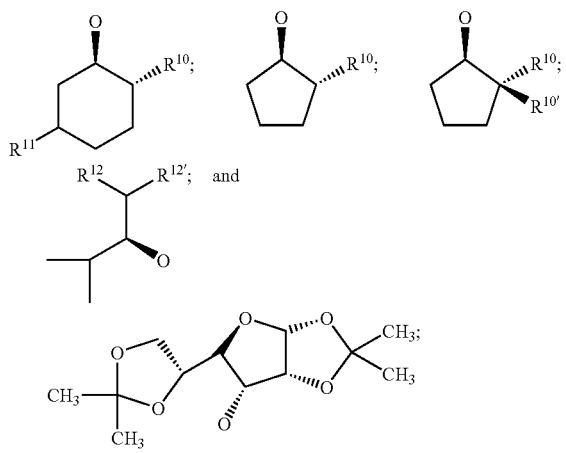

$R^{10}$ and $R^{10'}$ independently from each other are selected from the group consisting of:

(1) an aryl group, which is unsubstituted or substituted by phenyl; and (2) a $(C_3\text{-}C_{12})$alkyl group, which is unsubstituted or substituted by phenyl;

$R^{11}$ is selected from the group consisting of hydrogen and $(C_1\text{-}C_6)$alkyl; and $R^{12}$ and $R^{12'}$ independently from each other represent an aryl group.

The transformation of the compounds of formula (Va) into the compounds of formula (Vc) via the compounds of formula (Vb) as described previously, can also be carried out in a one step reaction, directly from the compounds of formula (Va) to the compounds of formula (Vc) without the intermediate of formula (Vb). Such modification of the reaction sequence as described previously is within the ordinary skill of an organic chemist.

Another preferred embodiment of the present invention is the process as described previously, wherein —$OR^9$ represents:

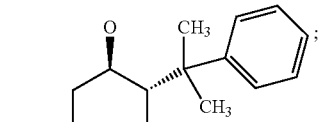

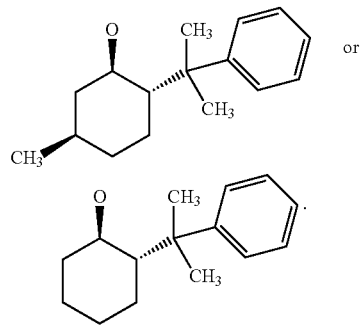

Another preferred embodiment of the present invention is the process as described previously, wherein —$OR^9$ represents:

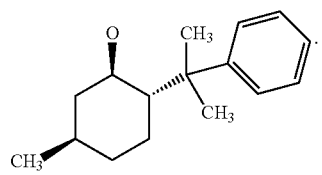

Still another preferred embodiment of the present invention is the process as described previously, wherein:

$R^{2'}$ and $R^{3'}$ are ethyl;

$R^{4'}$ is hydrogen or methyl; and —$OR^9$ is

The asymmetric reaction as described previously can also be carried out using the enantiomers of the alcohols $R^9OH$, which are designated R$^{18}$OH hereinafter, to furnish the enantiomer of the compound of formula (1a) which is designated 1b hereinafter.

Therefore, still another embodiment of the present invention is the process as described previously, for the manufacture of the compound of formula (1b):

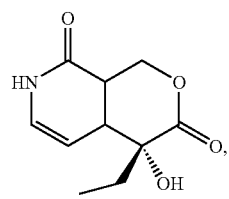
(1b)

comprising:
aaa) reacting the compound of formula (2):

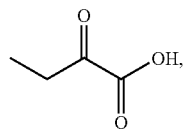
(2)

with a chiral secondary alcohol of the formula R$^{18}$OH to give an ester of formula (IIIb):

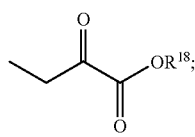
(IIIb)

bbb) further reacting said ester of formula (IIIb) with a compound of formula (IVa):

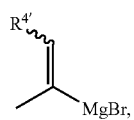
(IVa)

to obtain a compound of formula (Vd):

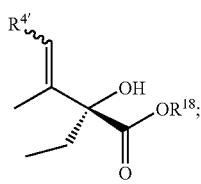
(Vd)

ccc) chemically cleaving the ester from the compound of formula (Vd) carried out in the presence of an alkali metal- or earth alkali metal hydroxide and optionally in the presence of hydrogen peroxide, to obtain the compound of formula (Ve):

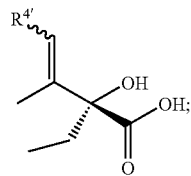
(Ve)

ddd) further reacting said compound of formula (Ve) in the presence of a tertiary amine and thionyl chloride, then subsequently adding an amine of formula HNR$^{2'}$R$^{3'}$ to obtain a compound of formula (Vf):

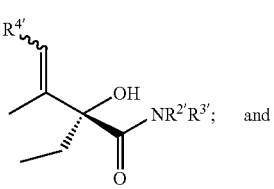
(Vf)

then performing the reaction steps steps d) to i) as described previously to obtain the compound of formula (1b);

wherein
R$^{2'}$, R$^{3'}$, R$^{4'}$, R$^{10}$, R$^{10'}$, R$^{11}$, R$^{12}$ and R$^{12'}$ have the meanings as defined previously; and wherein —OR$^{18}$ represents:

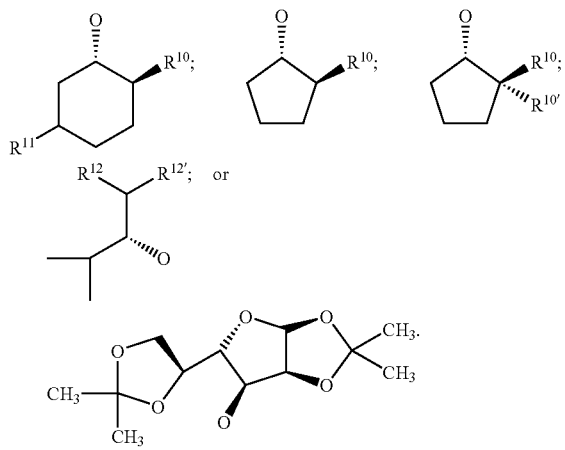

The transformation of the compounds of formula (Vd) into the compounds of formula (Vf) via the compounds of formula (Ve) as described previously, can also be carried out in a one step reaction, directly from the compounds of formula (Vd) to the compounds of formula (Vf) without the intermediate of formula (Ve). Such modification of the reaction sequence as described previously is within the ordinary skill of an organic chemist.

Another preferred embodiment of the present invention is the process as described previously, wherein —OR$^{18}$ represents:

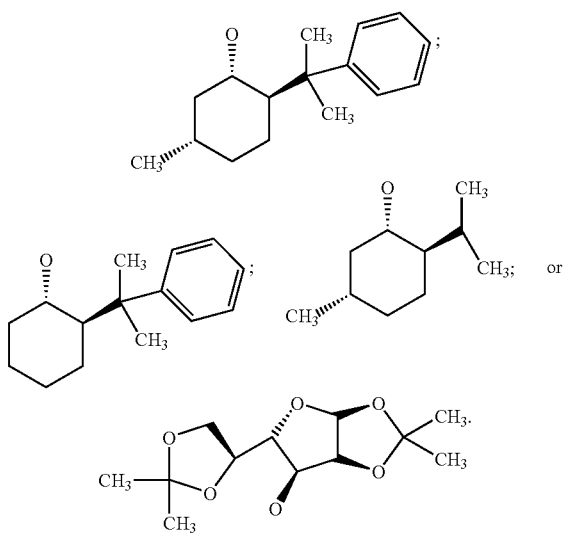

Another preferred embodiment of the present invention is the process as described previously, wherein —OR$^{18}$ represents:

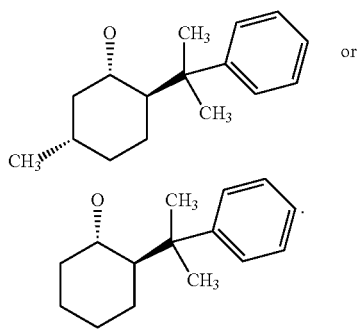

Another preferred embodiment of the present invention is the process as described previously, wherein:

R, R$^1$, R$^2$, R$^3$, R$^5$ and R$^6$ are ethyl; and

R$^4$, R$^7$ and R$^8$ are methyl.

Still another preferred embodiment of the present invention is the process as described previously, wherein the ethylbase of reaction step b) is ethyl magnesium bromide.

Still another preferred embodiment of the present invention is the process as described previously, wherein the reaction step b) is carried out in diethyl ether at temperatures between −30° C. and 0° C.

Still another preferred embodiment of the present invention is the process as described previously, wherein the reaction step c) is carried out in di-isopropyl ether at temperatures between −78° C. and −40° C.

Still another preferred embodiment of the present invention is the process as described previously, wherein the reaction step d) is carried out in the presence of dimethyl sulfide and at a temperature between −90° C. and −50° C.

Still another preferred embodiment of the present invention is the process as described previously, wherein the reaction step e) is carried out in ethanol and in the presence of cesium carbonate at temperatures between 0° C. and 40° C.

Still another preferred embodiment of the present invention is the process as described previously, wherein the reaction step f) is carried out in dimethylformamide and in the presence of dimethylformamide dimethylacetal at temperatures between 0° C. and 40° C.

Still another preferred embodiment of the present invention is the process as described previously, wherein the reaction step g) is carried out in dimethylformamide at temperature between 60° C. and 100° C.

Still another preferred embodiment of the present invention is the process as described previously, wherein the reaction step h) is carried out in the presence of sodium borohydride and cerium chloride at temperatures between 0° C. and 40° C.

Still another preferred embodiment of the present invention is the process as described previously, wherein said reaction step h) is carried out in ethanol and in the presence of excess sodium borohydride.

Still another preferred embodiment of the present invention is the process as described previously, wherein the reaction step i) is carried out in the presence of concentrated hydrochloric acid in dimethoxyethane at temperatures between 0° C. and 40° C.

Still another preferred embodiment of the present invention is the process as described previously, wherein the reaction step cc) is carried out in the presence of aqueous lithium hydroxide in methanol in a pressure tube, and at a temperature between 100° C. and 120° C.

Still another preferred embodiment of the present invention is the process as described previously, wherein the reaction step cc) is carried out in the presence of hydrogen peroxide.

Still another preferred embodiment of the present invention is the process as described previously, wherein the reaction step dd) is carried out in the presence of ethyl di-isopropylamine and thionyl chloride, and at a temperature between −40° C. and 0° C.

The reactions of steps aaa) to ddd) as defined herein can generally be carried out according to those of steps aa) to dd) as described previously.

In accordance with the present invention, the previously processes can generally be carried out according to the following specifications, wherein unless explicitly otherwise stated all substituents and definitions have the significances given previously.

Racemic Approach Towards the Compound of Formula (1):

The general reaction sequence as described previously starts from the dialkyl oxalate of formula (I), which is used to prepare α-ketoamides of formula (III) over two steps applying a modified literature procedure for steps a) and b) (M. A. Ciufolini, F. Roschangar, *Targets in Heterocyclic Systems*, 2000, 4, 25-55). Reaction step a) can be carried out using any amine of the formula HNR$^2$R$^3$ as defined previously. Preferably, said reaction step a) is carried out at temperatures between 40° C. and 140° C., more preferably between 80° C. and 100° C.

Reaction step b) is carried out in the presence of an ethyl base as defined previously, in an organic solvent such as alkanes or ethers, preferably diethyl ether, methyl tert-butyl ether or tetrahydrofuran and at temperatures between −78° C. and 35° C., preferably between −40° C. and room temperature, and more preferably between −30° C. and 0° C.

During the subsequent Grignard addition of step c), an (E/Z)-1-Methyl-1-alkenyl-magnesium bromide of formula (IV), preferably (E/Z)-1-Methyl-1-propenyl-magnesium bromide is added at temperatures between −100° C. and room temperature, preferably between −78° C. and 0° C., more preferably between −30° C. and 0° C., in suitable organic solvents, preferably in ethers, more preferably in tetrahydrofuran, diethyl ether, di-isopropyl ether or methyl tert-butyl ether. In reaction step d), ozonolysis of the C═C double bond in the compounds of formula (V) smoothly furnished the α-hydroxy-β-keto amides of formula (VI). This reaction is carried out in polar organic solvents, preferably in methanol, dichloromethane, ethyl acetate or pure acetic acid or aqueous mixtures of acetic acid, and at temperatures between −100° C. and room temperature, preferably between −90° C. and −50° C. When acetic acid is used, the reaction is preferably carried out at temperatures between 10° C. and 20° C. The five-membered, cyclic intermediate of the ozonolysis reaction is cleaved according to methods well known to the skilled artisan, preferably under conditions of reductive cleavage, more preferably using triphenylphosphine or dimethyl sulfide.

The subsequent reaction step e) is a tandem Knoevenagel condensation/lactonization reaction of the compounds of formula (VI) with the malonates of formula (VII), providing the α,β-unsaturated γ-lactones of formula (VIII). This reaction is preferably carried out in the presence of alkali metal carbonates or -hydrides as defined previously in suitable organic solvents such as lower alcohols, alkanes or ethers. Especially preferred is the use of methanol, ethanol or tetrahydrofuran. Said reaction step e) takes place at temperatures between −20° C. and 80° C., preferably between 0° C. and 40° C.

The reaction step f) is a condensation reaction of the compounds of formula (VIII) with tris(dialkylamino)methanes, preferably tris(dimethylamino)methane in dimethyl formamide furnishing the respective enamines of formula (IX). As an alternative reaction according to the present invention dialkylformamide dialkylacetals, preferably dimethyl formamide dimethylacetal (DMFDMA), can be used to replace the more expensive tris(dimethylamino)methane. Said reaction step f) takes place at temperatures between −20° C. and 100° C., preferably between 0° C. and 40° C.

In reaction step g) the crude compounds of formula (IX) are further reacted with ammonium acetate in dimethylformamide or acetic acid and at temperatures between room temperature and 160° C., preferably between 60° C. and 100° C., to result in the pyridones of formula (X).

The reaction step h) is the chemoselective reduction of the lactone ring in the compounds of formula (X) to give the diols of formula (XI). This reaction is accomplished by a modification of conditions previously reported by Ciufolini et al for a related, but different substrate (M. A. Ciufolini, F. Roschangar, *Tetrahedron* 1997, 53, 11049-11060). The reduction with alkali metal borohydrides as defined previously, preferably sodium borohydride, required Lewis acid activation by earth metal salts as defined previously. The use of chlorides, preferably cerium chloride, and an excess of sodium borohydride are especially preferred. The reduction did not run to completion even under these conditions and the crude product still contained 2 to 5% of both lactol diastereomers, which were efficiently removed by trituration with dichloromethane/methyl tert-butyl ether (2:1). Without cerium chloride, the reaction proceeded very slowly and resulted largely in decomposition of starting material of formula (X). Said reaction step h) takes place at temperatures between −20° C. and 80° C., preferably between 0° C. and 40° C.

The final reaction step i) is a cyclization reaction, giving rise to the α-hydroxylactone of formula (1). This reaction is preferably carried out at room temperature in the presence of concentrated mineral acids in ethereal solvents, preferably in dimethoxyethane, methyl tert-butyl ether, tetrahydrofuran and dioxane. Especially preferred according to the present invention is the use of concentrated hydrochloric acid in dimethoxyethane. The side products of this reaction are the respective ammonium halides, which result from the cleavage of the $NR^2R^3$-group during the cyclization reaction, especially diethylammonium chloride. Such side products can be removed by trituration with methanol, resulting in the purified racemic compound of formula (1) ("DE fragment") without any chromatographic purification. Said reaction step i) takes place at temperatures between −20° C. and 80° C., preferably between 0° C. and 40° C.

Asymmetric Approach: Synthesis of the Compound of Formula (1a):

The asymmetric version as described hereinbefore is mainly based on the racemic approach as described previously. The first reaction steps are different in such a way that they require a stereoselective synthesis of the respective (S)-enantiomers of the compounds of formula (VI). This is achieved starting from reaction step aa) with the preparation of enantiomerically pure α-ketoesters of the formula (IIIa) by reacting the 2-oxobutyric acid (2) with a chiral alcohol of the formula $R^9OH$, preferably (−)-8-phenylmenthol, as auxiliary reagent and according to conditions known from literature (D. L. Comins, M. F. Baevsky, H. Hong, *J. Am. Chem. Soc.* 1992, 114, 10971-10972). This reaction is carried out in the presence of aromatic solvents such as benzene, toluene, mesitylene or xylene, and in the presence of acids such as sulfuric acid or para-toluene sulfonic acid. The use of benzene and para-toluene sulfonic acid is especially preferred. Said reaction step aa) takes place at temperatures between 80° C. and 160° C., preferably between 80° C. and 130° C.

The following, stereodetermining reaction step bb) is a diastereoselective Grignard addition using an alkenyl magnesium bromide of formula (IVa), preferably isopropenyl magnesium bromide. Like the Grignard addition reaction under step c) above, the present reaction step also requires temperatures between −100° C. and room temperature, preferably between −90° C. and −60° C., as well as suitable organic solvents such as ethers, alkanes or aromatic solvents, preferably tetrahydrofuran, diethyl ether, di-isopropyl ether, methyl tert-butyl ether or toluene. The use of tetrahydrofuran is especially preferred.

The subsequent reaction step cc) is the cleavage of the auxiliary (chiral alcohol of formula $R^9OH$) in the presence of aqueous alkali metal- or earth alkali metal hydroxides such as lithium hydroxide, sodium hydroxide, potassium hydroxide, calcium hydroxide or barium hydroxide, preferably lithium hydroxide, and in the presence of hydrogen peroxide. The reaction takes place in suitable organic solvents such as lower alcohols and ethers, or mixtures thereof, preferably in methanol. This reaction requires heating in an autoclave to temperatures between room temperature and 180° C., preferably between 80° C. and 130° C., more preferably between 100° C. and 120° C. The separation of the resulting carboxylic acids of formula (Vb) and the auxiliary is achieved by pH-dependent extraction, thus allowing a facile recycling of the expensive chiral auxiliary, which can be reused several times.

The subsequent formation of the amides of formula (Vc) according to step dd) is based on a known protocol for the formation of related x-hydroxy amides derived from pyrrolidine (L. Tan, C.-y. Chen, W. Chen, L. Frey, A. O. King, R. D. Tillyer, F. Xu, D. Zhao, E. J. J. Grabowski, P. J. Reider, P. O'Shea, P. Dagneau, X. Wang, *Tetrahedron* 2002, 58, 7403-7410). In contrast to the known procedure, the present amide formation requires deprotonation of the carboxylic acids of formula (Vb), preferably by a tertiary amine, more preferably by ethyl di-isoproylamine, prior to the exposure to thionyl chloride. This reaction takes place at temperatures between −78° C. and 20° C., preferably between −40° C. and 0° C. The subsequent addition of the secondary amine of the formula HNR²R³' takes place at temperatures between −20° C. and 40° C., preferably between −10° C. and 30° C. Preferably this reaction is carried out in polar organic solvents like lower alcohols or alkyl halides, more preferably in dichloromethane.

Further reaction of the compounds of formula (Vc) towards the compound of formula (1a) can be carried out according to the reaction conditions described previously for reaction steps d) to i).

The reactions of steps aaa) to ddd) as defined herein only differ from the reaction steps aa) to dd) as defined previously by using the second enantiomeric forms of the respective chiral alcohols of formula R⁹OH, which enantiomeric forms are designated R¹⁸OH. Therefore, the reaction conditions of reactions aaa) to ddd) can generally be carried out according to those of steps aa) to dd) as described previously.

Subsequent Synthesis of Camptothecin and Derivatives Thereof

Subsequent to the synthesis of the compound of formula (1), (1a) or (1b) according to the present invention, the final reaction steps in order to obtain racemic, (R)- or (S)-camptothecin, or derivatives thereof, require the coupling of the compound of formula (1), (1a) or (1b) to the quinoline derivative (5, scheme 2) via a Mitsunobu-alkylation and subsequent Heck-cyclisation (D. L. Comins, H. Hong, J. K. Saha, G. Jinkua, *J. Org. Chem* 1994, 59, 5120-5121; or D. L. Comins, H. Hong, J. K. Saha, G. Jinkua, *Tetrahedron Lett* 1994, 35, 5331-5334). This procedure can generally be performed under the conditions which are suitable for said Mitsunobu-alkylation and said Heck-cyclisations, and which are well known to the person skilled in the art.

One preferred example of suitable reaction conditions for said reactions is given by the synthesis route described in scheme 2. The synthesis according to scheme 2 leads to (S)-camptothecin, but can also be carried out as a racemic route to provide (rac)-camptothecin, or starting from (1b) to furnish (R)-camptothecine. It is understood that such modifications are within the ordinary knowledge of the skilled artisan, and therefore need not to be further exemplified in all details.

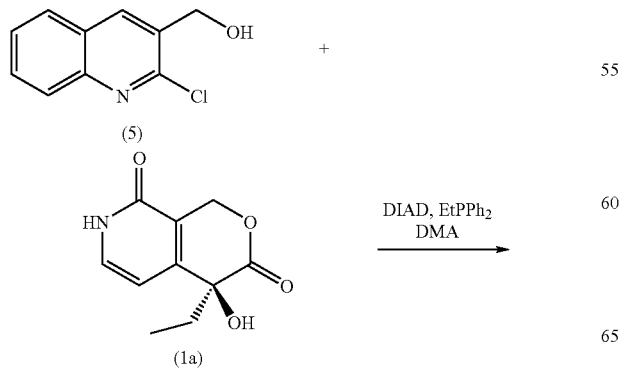

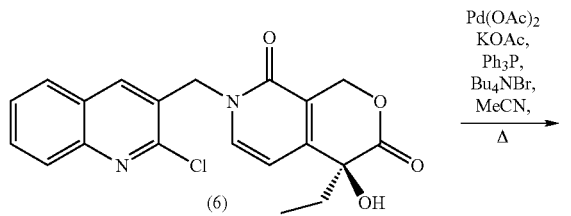

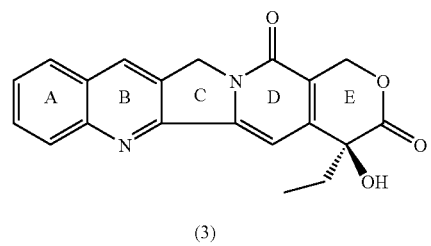

The "AB-ring" of formula (3) can be optionally substituted. It is within the ordinary knowledge of the person skilled in the art that the process according to the present invention can also be used in the manufacture of derivatives of formula (3) wherein the "AB-ring" is further substituted.

Consequently a further embodiment of the present invention is the process as described previously, wherein said compound of formula (1a) is transformed into a compound of formula (A):

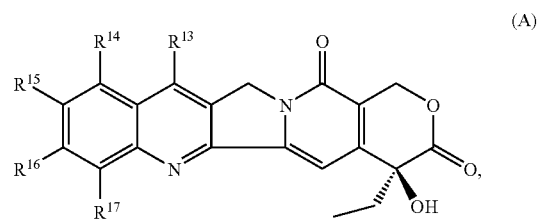

by:

a) further reacting said compound of formula (1a) with a compound of formula (B):

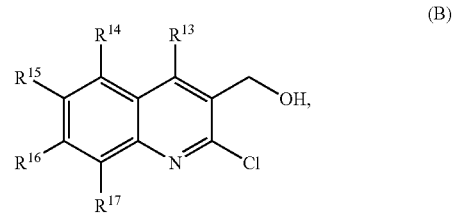

in the presence of diisopropyl azodicarboxylate (DIAD), ethyldiphenylphosphine (EtPPh$_2$) and dimethylacetamide (DMA), to give a compound of formula (C):

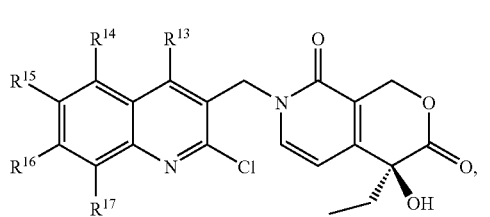

and b) further reacting said compound of formula (C) with palladium (II) acetate (Pd(OAc)$_2$), potassium acetate (KOAc), triphenylphosphine (Ph$_3$P), tetrabutyl ammonium bromide (Bu$_4$NBr) and acetonitrile(MeCN) to give the corresponding compound of formula (A), wherein:

$R^{13}$, $R^{14}$, $R^{15}$, $R^{16}$ and $R^{17}$ are independently selected from the group consisting of: hydrogen; halogen; cyano; (C$_1$-C$_6$)alkyl; —O—(C$_1$-C$_6$)alkyl; —S—(C$_1$-C$_6$)alkyl; hydroxyl; amino; mono (C$_1$-C$_6$)alkyl amino; di(C$_1$-C$_6$)alkyl amino; nitro; and trifluoromethyl. In addition, $R^{13}$ and $R^{14}$ together with the carbon atoms to which they are attached can also form a six-membered, unsaturated cyclic hydrocarbon, wherein one or two carbon atoms are optionally replaced be nitrogen and which is unsubstituted or once substituted by (C$_1$-C$_6$)alkyl.

Still another embodiment of the present invention is the process as described previously, wherein the compound of formula (1) is transformed into a compound of formula (A-1):

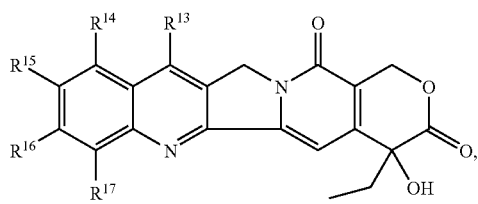

by:

a) further reacting said compound of formula (1) with a compound of formula (B) as defined above:

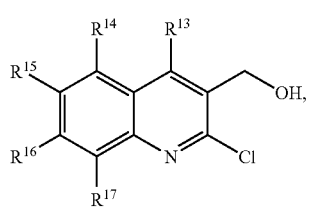

in the presence of diisopropyl azodicarboxylate (DIAD), ethyldiphenylphosphine (EtPPh$_2$) and dimethylacetamide (DMA), to give a compound of formula (C-1):

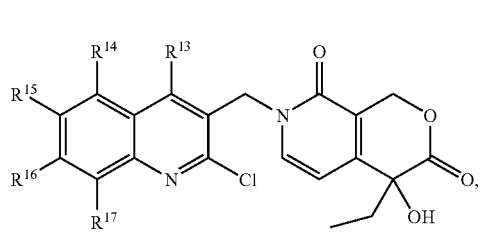

and b) further reacting said compound of formula (C-1) with palladium (II) acetate (Pd(OAc)$_2$), potassium acetate (KOAc), triphenylphosphine (Ph$_3$P), tetrabutyl ammonium bromide (Bu$_4$NBr) and acetonitrile(MeCN) to give the corresponding compound of formula (A-1), wherein $R^{13}$, $R^{14}$, $R^{15}$, $R^{16}$ and $R^{17}$ have the significances given previously.

A further embodiment of the present invention is the process as described previously, wherein said compound of formula (1b) is transformed into a compound of formula (A-2):

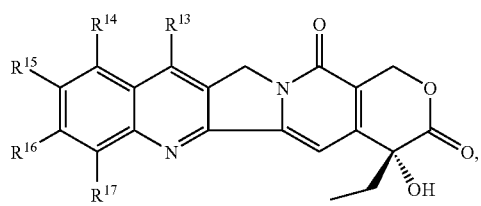

by:

a) further reacting said compound of formula (1b) with a compound of formula (B) as defined above:

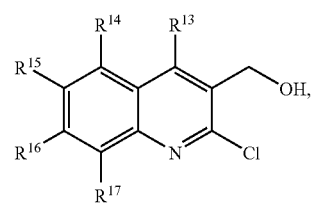

in the presence of diisopropyl azodicarboxylate (DIAD), ethyldiphenylphosphine (EtPPh$_2$) and dimethylacetamide (DMA), to give a compound of formula (C-2):

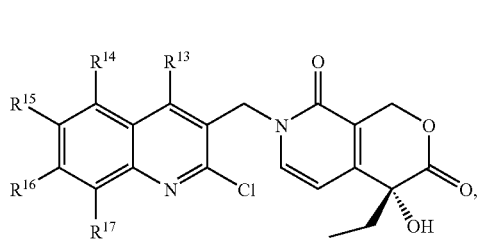
(C-2)

and b) further reacting said compound of formula (C-2) with palladium (II) acetate (Pd(OAc)$_2$), potassium acetate (KOAc), triphenylphosphine Ph$_3$P), tetrabutyl ammonium bromide (Bu$_4$NBr) and acetonitrile(MeCN) to give the corresponding compound of formula (A-2), wherein $R^{13}$, $R^{14}$, $R^{15}$, $R^{16}$ and $R^{17}$ have the significances given previously.

Still another embodiment of the present invention is the process as described previously wherein the compound of formula (1a) is transformed into the compound of formula (3a):

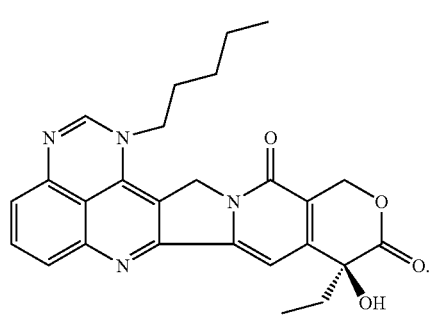
(3a)

Still another embodiment of the present invention is the process as described previously wherein the compound of formula (1a) is transformed into the compound of formula (3):

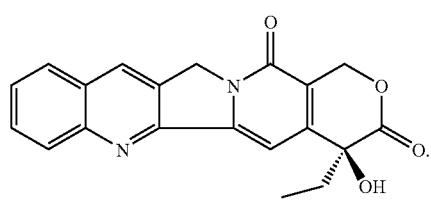
(3)

Still another embodiment of the present invention is the process as described previously wherein the compound of formula (1b) is transformed into the compound of formula (3b):

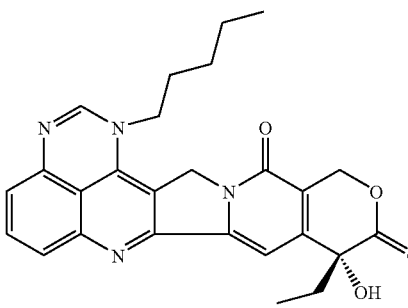
(3b)

Still another embodiment of the present invention is the process as described previously wherein the compound of formula (1b) is transformed into the compound of formula (3c):

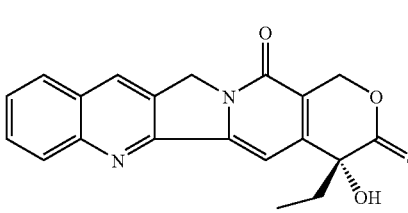
(3c)

Another embodiment of the present invention is a compound of formula (A) or a salt thereof made by the process described previously for the manufacture of compounds of formula (A).

Another embodiment of the present invention is a compound of formula (A-1) or a salt thereof made by the process described previously for the manufacture of compounds of formula (A-1).

Another embodiment of the present invention is a compound of formula (A-2) or a salt thereof made by the process described previously for the manufacture of compounds of formula (A-2).

Another embodiment of the present invention is a compound of formula (3a) or a salt thereof made by the process described previously for the manufacture of compounds of formula (3a).

Another embodiment of the present invention is a compound of formula (3) or a salt thereof made by the process described previously for the manufacture of compounds of formula (3).

Another embodiment of the present invention is a compound of formula (3b) or a salt thereof made by the process described previously for the manufacture of compounds of formula (3b).

Another embodiment of the present invention is a compound of formula (3c) or a salt thereof made by the process described previously for the manufacture of compounds of formula (3c).

Another embodiment of the present invention is camptothecin or a derivative thereof made by a process using the compound (1) described previously as made by a process described previously.

Another embodiment of the present invention is a pharmaceutical composition comprising a therapeutically effective amount of the camptothecin compound above and a pharmaceutically acceptable carrier.

Camptothecin, derivatives thereof, and the compounds of formulae (A), (A-1), (A-2), (3), (3a), (3b), and (3c) or their pharmaceutically acceptable salts made by the processes described previously can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions. Such pharmaceutical compositions may be used for the inhibition of tumor growth or for the treatment of cancer.

The above-mentioned pharmaceutical compositions can be obtained by processing camptothecin, derivatives thereof, and the compounds of formulae (A), (A-1), (A-2), (3), (3a), (3b), and (3c) or their pharmaceutically acceptable salts (made by the processes described herein) with pharmaceutically inert, inorganic or organic carriers. For example, lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance, carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

The following examples are provided to aid the understanding of the present invention. It is understood that modifications can be made without departing from the spirit of the invention.

If not explicitly otherwise stated, the following abbreviations are used and have the following meanings:

min refers to minute(s)
h refers to hour(s)
rt refers to room temperature
NMR refers to nuclear magnetic resonance
GC refers to gas chromatography
TLC refers to thin layer chromatography
HPLC refers to high performance liquid chromatography
dr refers to distereosiomer ratio
er refers to enantiomer ratio
ee refers to enantiomeric excess
mp refers to melting point

EXAMPLES

Example 1

Synthesis of N,N-diethyl-oxalamic acid ethyl ester (8)

To 30.00 g (203.2 mmol) diethyloxalate (7) were added at room temperature 42.2 mL diethylamine (406.4 mmol, 2.0 eq). The colorless clear solution was heated to reflux (oil bath temperature: 90° C.) and the reaction was monitored by HPLC. After 2.5 h, the resulting yellow-orange liquid was cooled to room temperature and all volatile compounds (ethanol, diethylamine) were removed in a rotary evaporator (50° C., 10 mbar) furnishing the crude product (35.073 g, 100% by weight) as a yellow liquid. Purification was achieved using a high vacuum distillation (bp 85° C. at 0.08 mbar) furnishing the title compound (30.22 g, 174.4 mmol, 86% by weight) as colorless liquid.

$^1$H NMR (300 MHz, CDCl$_3$): δ 4.34 (q, 2H, J=7.1 Hz), 3.43 (q, 2H, J=7.2 Hz), 3.29 (q, 2H, J=7.2 Hz), 1.37 (t, 3H, J=7.1 Hz), 1.23 (t, 3H, J=7.1 Hz), 1.19 (t, 3H, J=7.1 Hz) ppm.

Example 2

Synthesis of N,N-diethyl-2-oxo butyramide (9)

mL ethyl magnesium bromide solution (191.8 mmol, 1.10 eq) were diluted with 182.6 mL diethylether. The solution was cooled to −15° C. and a solution of 30.20 g of compound (8) as obtained from example 1 (174.4 mmol) in 60.4 mL diethylether was added dropwise. The resulting viscous suspension was stirred for additional 75 min at −15° C. Subsequently, the reaction was quenched by addition of 14.96 mL acetic acid (261.6 mmol, 1.5 eq). Then, 35 mL water were added to dissolve all salts and the cooling bath was removed. After 15 min, the mixture was washed twice with 200 mL, pH-7-buffer and the organic phase was dried over 20 g sodium sulfate and was filtered. The filter cake was washed with 40 mL diethylether. After evaporation of solvent in a rotary evaporator (40° C./10 mbar), the crude product (26.33 g, 96% by weight) was obtained as a yellow liquid. Purification was achieved using a high vacuum distillation (bp 86° C. at 2.5 mbar) furnishing the title compound (18.66 g, 118.7 mmol, 68% by weight) as colorless liquid.

$^1$H NMR (300 MHz, CDCl$_3$): δ 3.40 (q, 2H, J=7.1 Hz), 3.25 (q, 2H, J=7.2 Hz), 2.78 (q, 2H, J=7.3 Hz), 1.12-1.18 (m, 9H, J=7.0 Hz, J=7.0 Hz) ppm.

Example 3

Synthesis of 2-ethyl-2-hydroxy-3-methyl-pent-3-enoic acid diethylamide (10)

500 mL 1-methyl-1-propenyl magnesium bromide solution (250.0 mmol, 3.0 eq) were cooled to −78° C. prior to slow addition of a precooled solution (−78° C.) of 13.10 g of compound (9) as obtained from example 2 (83.2 mmol) in 262 mL diisopropylether via a canula. After 60 min, 250 mL saturated aqueous ammonium chloride were added and the mixture was extracted 3 times with 250 mL, dichloromethane. The combined organic phases were dried over 25 g sodium sulfate and filtered. The filter cake was washed with 50 mL dichloromethane. After removal of solvent in a rotary evaporator (40° C., 10 mbar), the crude product (18.05 g, 102% by weight) was obtained as a yellow liquid, which was purified by high vacuum distillation (bp 65° C. at 0.28 mbar) furnishing the title compound (8.145 g, 38.18 mmol) as light yellow liquid in form of E/Z isomers (E/Z=5.1:1). An analytical sample of the (E) -isomer was obtained by column chromatography with hexane/ethyl acetate (4:1).

$^1$H NMR (300 MHz, CDCl$_3$): δ 5.68 (m, 1H), 5.28 (s, 1H), 3.40 (m, 4H), 1.96 (dq, 1H, J=13.8 Hz, J=7.5 Hz), 1.87 (dq, 1H, J=13.7 Hz, J=7.2 Hz), 1.67 (d, 3H, J=6.8 Hz), 1.57 (br. s, 3H), 1.15 (t, 3H, J=6.8 Hz), 1.08 (t, 3H, J=6.9 Hz), 0.86 (t, 3H, J=7.3 Hz) ppm;

$^{13}$C NMR (100 MHz, CDCl$_3$) of the (E)-isomer: δ 173.0, 137.7, 120.1, 78.5, 41.4, 41.2, 28.1, 13.5, 13.3, 12.8, 12.4, 8.0 ppm.

Example 4

Synthesis of 2-N,N-triethyl-2-hydroxy-3-oxo-butyramide (11)

Through a stirred solution of 8.000 g of compound (10) as obtained from example 3 (37.50 mmol) in 400 mL dichloromethane at −78° C., ozone was bubbled (150 L/h) until a blue colour appeared. Subsequently, argon was bubbled through the solution for 10 min. 28 mL dimethylsulfide (375 mmol, 10.0 eq) were subsequently added and the solution was allowed to slowly warm up to room temperature overnight. The mixture was washed three times with 250 mL water. The organic phase was dried over 20 g sodium sulfate and was filtered. The solid was washed with 40 mL dichloromethane. After evaporation of solvent in a rotary evaporator (40° C./10 mbar), the crude product (7.85 g, 104% by weight) was obtained as a yellow oil.

$^1$H NMR (300 MHz, CDCl$_3$): δ 5.19 (s, 1H), 3.41 (m, 2H), 3.29 (q, 2H, J=7.1 Hz), 2.19 (s, 3H), 2.01 (dq, 1H, J=14.7 Hz, J=7.4 Hz), 1.96 (dq, 1H, J=15.3 Hz, J=7.2 Hz), 1.15 (t, 3H, J=7.0 Hz), 1.12 (t, 3H, J=7.0 Hz), 0.83 (t, 3H, J=7.5 Hz) ppm;

$^{13}$C NMR (100 MHz, CDCl$_3$): δ 208.2, 170.2, 84.8, 43.1, 42.9, 28.9, 26.1, 15.0, 13.6, 8.6 ppm.

Example 5

Synthesis of 5-diethylcarbamoyl-5-ethyl-4-methyl-2-oxo-2,5-dihydro-furan-3-carboxylic acid ethyl ester (12)

To a solution of 2.500 g of compound (11) as obtained from example 4 (12.42 mmol) and 9.73 mL diethylmalonate (62.10 mmol, 5.0 eq) in 100 mL ethanol were added at room temperature, 16.27 g cesium carbonate (49.68 mmol, 4.0 eq). After 26 h the yellow suspension was cooled to 0° C. and 200 mL aqueous hydrochloric acid (0.5 M, 65.25 mmol, 5.0 eq) were added dropwise over 60 min. 95 mL ethanol were subsequently removed in a rotary evaporator (50° C., 5 mbar) and then, 200 mL ethylacetate were added. The organic phase was washed twice with 150 mL brine, dried over 20 g sodium sulfate and filtered. The filter cake was washed with 40 mL ethylacetate. After evaporation of the solvent in a rotary evaporator (50° C., 5 mbar), volatile components were removed in a Kugelrohr apparatus (55° C., 0.08 mbar). The crude product (6.758 g, 183% by weight) was obtained as a yellow liquid.

$^1$H NMR (300 MHz, CDCl$_3$): δ 4.36 (q, 2H, J=7.1 Hz), 3.58 (m, 1H), 3.12-3.48 (m, 3H), 2.50 (s, 3H), 2.35 (dq, 1H, J=14.4 Hz, J=7.1 Hz), 2.00 (dq, 1H, J=14.4 Hz, J=7.3 Hz), 1.38 (t, 3H, J=7.1 Hz), 1.21 (m, 3H), 1.15 (m, 3H), 0.86 (t, 3H, J=7.4 Hz) ppm;

$^{13}$C NMR (100 MHz, CDCl$_3$): δ 177.0, 166.5, 164.8, 160.5, 119.0, 90.9, 60.8, 42.2, 42.1, 29.1, 14.5, 13.8, 13.4, 11.8, 6.5 ppm.

Example 6

Synthesis of 5-diethylcarbamoyl-4-((E)-2-dimethylamino-vinyl)-5-ethyl-2-oxo-2,5-dihydro-furan-3-carboxylic acid ethyl ester (13)

To a solution of 500.0 mg of compound (12) as obtained from example 5 (22.73 mmol) in 3.0 mL dimethyl formamide were added at room temperature 3.0 mL tris(dimethylamino) methane (17.3 mmol, 10.3 eq). The color of the reaction mixture changed from orange to brown and further to green. After 17 h, the mixture was diluted with 50 mL dichloromethane, washed with 25mL aqueous hydrochloric acid (1.0 M) and washed again three times with 50 mL brine. The organic phase was dried over 2 g sodium sulfate and was filtered. The filter cake was washed with 4 mL dichloromethane. After evaporation of the solvent in a rotary evaporator (50° C., 5 mbar), the crude product was obtained as an orange oil (627.0 mg, 106% by weight), which was liberated from residual dimethyl formamide in a high vacuum rotary evaporator (50° C., 0.5 mbar) yielding the title product (536.0 mg, 1.517 mmol, 90% by weight) as orange crystals. Mp: 105° C.;

$^1$H NMR (300 MHz, CDCl$_3$): δ 7.97 (br., 1H), 6.47 (br., 1H), 4.32 (m, 2H), 3.52 (dq, 1H, J=13.2 Hz, J=6.6 Hz), 3.18 (s, 3H), 3.17 (m, 2H), 3.00 (s, 3H), 2.99 (m, 1H), 2.41 (dq, 1H, J=14.3 Hz, J=7.0 Hz), 2.03 (dq, 1H, J=14.3 Hz, J=7.1 Hz), 1.39 (t, 3H, J=7.1 Hz), 1.20 (t, 3H, J=7.0 Hz), 1.08 (t, 3H, J=7.0 Hz), 0.84 (t, 3H, J=7.3 Hz) ppm;

$^{13}$C NMR (100 MHz, CDCl$_3$): δ 171.8, 169.6, 168.0, 164.4, 154.3, 99.3, 91.9, 87.7, 60.1, 45.7, 43.0, 42.4, 36.8, 34.6, 14.4, 14.0, 12.3, 7.3 ppm.

Example 7

Alternative synthesis of 5-diethylcarbamoyl-4-((E)-2-dimethylamino-vinyl)-5-ethyl-2-oxo-2,5-dihydro-furan-3-carboxylic acid ethyl ester (13) using DMFDMA To a solution of 6.758 g of compound (12) as obtained from example 5 (22.73 mmol) in 40 mL dimethyl formamide were added at room temperature 40 mL dimethyl formamide dimethylacetal (DMFDMA, 285.1 mmol, 12.5 eq). The color of the reaction mixture changed from orange to brown and further to green. After 2.5 h, the mixture was diluted with 150 mL dichloromethane and washed with 150 mL aqueous hydrochloric acid (1.0 M) and subsequently three times with 150 mL brine. The organic phase was dried over 20 g sodium sulfate and was filtered. The filter cake was washed with 40 mL dichloromethane. After evaporation of the solvent in a rotary evaporator (50° C., 5 mbar), the crude product was obtained as a red-brown liquid.

Example 8

Synthesis of 1-ethyl-3,4-dioxo-1,3,4,5-tetrahydro-furo[3,4-c]pyridine-1-carboxylic acid diethylamide (14)

To a solution of 10.63 g of compound (13) as obtained from example 6 or 7 (29, 30.17 mmol) in 85 mL dimethyl formamide were added at room temperature 23.7 g ammonium acetate (301.7 mmol, 10.0 eq) resulting in the formation of a shiny red solution, which was heated to 80° C. After 19.25 h, the mixture was diluted with 150 mL dichloromethane and successively washed with 130 mL water, 130 mL aqueous hydrochloric acid (0.5 M) and subsequently three times with 130 mL brine. The organic phase was dried over 20 g sodium sulfate and was filtered. The filter cake was washed with 40 mL dichloromethane. After evaporation of the solvent in a rotary evaporator (50° C., 5 mbar), the crude product was obtained as a red liquid (6.611 g, 79% by weight). All volatile components were removed in a Kugelrohr distillation apparatus. The residue was purified by trituration for 18 h at room temperature with 12 mL heptane /methyl tert-butyl ether (1:1), then with 8 mL heptane/methyl tert-butyl ether (1:1) and finally with 10 mL methyl tert-butyl ether furnishing the title compound (1.797 g, 6.46 mmol, 21% by weight), as violet crystals.

Mp: 177° C.;

$^1$H NMR (300 MHz, CDCl$_3$): δ 13.03 (br. s, 1H), 7.78 (d, 1H, J=6.6 Hz), 6.93 (d, 1H, J=6.6 Hz), 3.94 (dq, 1H, J=13.7 Hz, J=7.4 Hz), 3.50 (dq, 1H, J=13.4 Hz, J=7.0 Hz), 3.28 (dq, 1H, J=14.3 Hz, J=7.2 Hz), 3.17 (dq, 1H, J=13.6 Hz, J=7.0 Hz), 2.39 (dq, 1H, J=14.5 Hz, J=7.4 Hz), 2.09 (dq, 1H, J=14.4 Hz, J=7.3 Hz), 1.24 (t, 3H, J=6.9 Hz), 1.14 (t, 3H, J=6.9 Hz), 0.89 (t, 3H, J=7.3 Hz) ppm;

$^{13}$C NMR (100 MHz, CDCl$_3$): δ 169.2, 166.6, 166.2, 160.3, 141.9, 112.7, 104.5, 89.0, 42.7, 31.7, 14.7, 12.4, 7.6 ppm.

Example 9

Synthesis of N,N-diethyl-2-hydroxy-2-(3-hydroxymethyl-2-oxo-1,2-dihydro-pyridin-4-yl)-butyramide (15)

To a solution of 1.000 g of compound (14) as obtained from example 8 (3.595 mmol) in 40 mL ethanol were added at room temperature 2.215 g cerium (III) chloride (grinded, 8.99 mmol, 2.5 eq). The suspension was placed in an ultrasonic bath for 10 min and was then cooled to 15° C. by a water bath. 2.40 g sodium borohydride (61.1 mmol, 17 eq) were added in 6 portions over 3 h. After additional 2 h at room temperature, the suspension was poured onto 800 mL saturated aqueous sodium hydrogencarbonate/brine (1:1) and the mixture was vigorously stirred for 13 h prior to extraction with five times 400 mL, dichloromethane/ethanol (4:1). The combined organic extracts were evaporated in a rotary evaporator (50° C., 5 mbar). The crude product was obtained as a purple-red solid (879.6 mg, 87% by weight), which was purified by trituration with 5.25 mL dichloromethane/methyl tert-butyl ether (2:1) yielding the title compound (623.2 mg, 2.21 mmol, 61% by weight) as a white solid.

Mp: 193° C.;

$^1$H NMR (300 MHz, DMSO): δ 11.68 (br. s, 1H), 7.32 (d, 1H, J=7.1 Hz), 6.41 (d, 1H, J=7.0 Hz), 6.06 (s, 1H), 4.68 (t, 1H, J=5.9 Hz), 4.37 (d, 2H, J=5.9 Hz), 3.05-3.40 (m, 4H), 2.07 (dq, 1H, J=14.3 Hz, J=7.3 Hz), 1.86 (dq, 1H, J=14.3 Hz, J=7.3 Hz), 1.01 (t, 3H, J=7.0 Hz), 0.74 (t, 3H, J=7.0 Hz), 0.68 (t, 3H, J=7.4 Hz) ppm;

$^{13}$C NMR (100 MHz, DMSO): δ 171.5, 163.3, 152.5, 132.3, 126.8, 103.8, 77.9, 55.6, 40.9, 32.8, 12.6, 12.2, 7.5 ppm.

Example 10

Synthesis of 4-ethyl-4-hydroxy-1,7-dihydro-4H-pyrano[3,4-c]pyridine-3,8-dione (16)

To a suspension of 560.0 mg of compound (15) as obtained from example 9 (1.983 mmol) in 11.2 mL dimethoxyethane were added dropwise at 0° C. 1.68 mL concentrated aqueous hydrochloric acid (36.5%) (19.83 mmol, 10.0 eq). The ice bath was removed after 15 min and the triphasic mixture was vigorously stirred. After 4 h, the mixture was evaporated to dryness in a rotary evaporator (27° C., 5 mbar, then 1 mbar). The crude product was obtained as a lightly yellow semisolid (805.4mg, 194% by weight).333.3 mg crude product were purified by trituration with 0.7 mL methanol at room temperature for 18 h furnishing the title compound (168.7 mg, 0.425 mmol, 98% by weight) as white crystals.

Mp: 227° C. (decomposition).

$^1$H NMR (300 MHz, CDCl$_3$/MeOH (1:1)): δ 7.18 (d, 1H, J=6.8 Hz), 6.44 (d, 1H, J=7.0 Hz), 5.31 (d, 1H, J=16.2 Hz), 4.97 (d, 1H, J=16.2 Hz), 1.65 (m, 2H), 0.76 (t, 3H, J=7.3 Hz) ppm;

$^{13}$C NMR (100 MHz, DMSO): δ 171.9, 158.2, 149.2, 134.0, 118.4, 101.4, 71.3, 64.5, 29.8, 7.0 ppm.

Example 11

Synthesis of 2-oxo-butyric acid (1R,2S,5R)-5-methyl-2-(1-methyl-1-phenyl-ethyl)-cyclohexyl ester (17)

A solution of 2.28 g 2-oxobutyric acid (2, 22.11 mmol, 1.3 eq), 4.04 g (−)-8-phenylmenthol (18, 17.02 mmol, 1.0 eq) and 169.9 mg para-toluenesulfonic acid monohydrate (0.884 mmol, 0.52 eq) in 48 mL benzene was heated to reflux for 20 h 35 min. After cooling down to room temperature, the solution was washed twice with 50 mL saturated aqueous sodium hydrogencarbonate solution, and subsequently with 50 mL water and 50 mL brine. The organic phase was dried over 5 g sodium sulfate and was filtered. The filter cake was washed with 10 mL benzene. The organic phase was evaporated to dryness in a rotary evaporator (40° C., 20 mbar) yielding the title compound (4.98 g, 92% by weight) as colorless solid.

$[α]_D^{20}$ (c=0.827 g/dL, CHCl$_3$)=+1.3;

$^1$H NMR (300 MHz, CDCl$_3$): δ 7.19-7.27 (m, 4H), 7.09 (m, 1H), 4.95 (td, 1H, J=10.7 Hz, J=4.5 Hz), 2.36 (dq, 1H, J=19.4 Hz, J=7.1 Hz), 2.19 (dq, 1H, J=19.4 Hz, J=7.1 Hz), 2.14 (m, 1H), 1.84 (m, 2H), 1.69 (m, 1H), 1.50 (m, 1H), 1.31 (s, 3H), 1.22 (s, 3H), 1.10-1.40 (m, 3H), 0.94 (t, 3H, J=7.1 Hz), 0.89 (d, 3H, J=6.4 Hz) ppm.

Example 12

Synthesis of (2S)-2-ethyl-2-hydroxy-3-methyl-but-3-enoic acid (1R,2S,5R)-5-methyl-2-(1-methyl-1-phenyl-ethyl)-cyclohexyl ester (19)

To a solution of 4.200 g of compound (17) as obtained from example 11 (13.27 mmol) in 168 mL tetrahydrofuran were added dropwise at −78° C. 39.8 mL isopropenylmagnesium bromide (19.91 mmol, 1.5 eq). After additional 50 min, the reaction mixture was quenched by addition of 110 mL saturated aqueous ammonium chloride solution, and was extracted twice with 110 mL ethyl acetate. The combined organic phases were washed with 110 mL brine, dried over 15 g sodium sulfate and were filtered. The filter cake was washed with 30 mL ethyl acetate. The organic phase was evaporated to dryness in a rotary evaporator (40° C., 8 mbar) yielding the title compound (4.790 g, 101% by weight, dr=93:7)as a yellow oil.

$[\alpha]_D^{20}$ (c=0.615 g/dL, CHCl$_3$)=−44.0;

$^1$H NMR (300 MHz, CDCl$_3$): δ 7.15-7.29 (m, 5H), 5.11 (br. s, 1H), 4.97 (m, 1H), 4.84 (td, 1H, J=10.8 Hz, J=4.2 Hz), 2.83 (br. s, 1H), 2.09 (m, 1H), 1.97 (m, 1H), 1.74 (s, 3H), 1.31 (s, 3H), 1.21 (s, 3H), 0.90-1.80 (m, 8H), 0.87 (d, 3H, J=6.4 Hz), 0.80 (t, 3H, J=7.4 Hz) ppm;

$^{13}$C NMR (100 MHz, CDCl$_3$): δ 173.9, 151.0, 144.5, 128.2, 125.4, 125.4, 113.1, 79.7, 77.8, 49.9, 41.0, 39.9, 34.5, 31.4, 28.8, 27.3, 27.1, 26.4, 21.7, 19.3, 7.8 ppm.

Example 14

Synthesis of (S)-2-ethyl-2-hydroxy-3-methyl-but-3-enoic acid (20)

A solution of 3.025 g of compound (19) as obtained from example 12 (8.435 mmol) in 40 mL methanol/tetrahydrofuran (1:1) was treated with 16.9 mL aqueous lithium hydroxide (1.0 M, 16.9 mmol, 2.0 eq). The resulting colorless suspension was heated to 110° for 18.5 h providing a slightly brown solution. After cooling down to room temperature, the reaction mixture was diluted with 150 mL methyl tert-butyl ether and 150 mL aqueous lithium hydroxide. The aqueous phase was extracted one more time with 150 mL methyl tert-butyl ether to remove the auxiliary (−)-8-phenylmenthol.

Subsequently, the aqueous phase was adjusted to pH 2 by addition of 10% aqueous potassium hydrogensulfate. The aqueous phase was extracted four times with 100 mL of a mixture of chloroform/ethanol (4:1). The combined organic phases were evaporated to dryness in a rotary evaporator (40° C., 10 mbar) and the title compound (931.4 mg, 77% by weight) was obtained as a yellow solid.

$[\alpha]_D^{20}$ (c=0.251 g/dL, CHCl$_3$)=−11.9;

mp: 77° C.;

$^1$H NMR (300 MHz, CDCl$_3$): δ 5.26 (s, 1H), 5.06 (br. s, 1H), 2.04 (dq, 1H, J=14.2 Hz, J=7.2 Hz), 2.04 (dq, 1H, J=14.3 Hz, J=7.4 Hz), 1.85 (s, 3H), 0.94 (t, 3H, J=7.4 Hz) ppm;

$^{13}$C NMR (100 MHz, CDCl$_3$): δ 179.4, 144.3, 113.5, 79.9, 29.1, 19.1, 7.7 ppm.

Example 15

Synthesis of (S)-2-ethyl-2-hydroxy-3-methyl-but-3-enoic acid diethylamide (21)

To a solution of 1.000 g of compound (20) as obtained from example 14 (6.95 mmol) in 30 mL dichloromethane were added dropwise at −15° C. 2.5 mL N-ethyldiisopropyl amine (14.60 mmol, 2.1 eq) and after additional 8 min. 1.53 mL thionyl chloride (20.85 mmol, 3.0 eq). After 50 min., a solution of 7.22 mL diethylamine (69.5 mmol, 10.0 eq) in 20 mL dichloromethane was added dropwise using a syringe pump (addition time: 60 min.). The reaction mixture was allowed to slowly warm up to room temperature overnight. The reaction mixture was diluted with 50 mL dichloromethane and was then washed with 50 mL aqueous hydrochloric acid (1.0 M). The organic phase was dried over 5 g sodium sulfate and was filtered. The solid was washed with 10 mL dichloromethane. After evaporation of solvent in a rotary evaporator (40° C./10 mbar), the crude product (1.36 g, 98% by weight) was obtained as a yellow oil, which was purified by column chromatography with heptane/ethyl acetate (9:1) yielding the title compound (0.900 g, 4.515 mmol, 65% by weight, er=93.4: 6.6) as yellow oil.

$[\alpha]_D^{20}$ (c=0.990 g/dL, CHCl$_3$)=+63.3;

$^1$H NMR (300 MHz, CDCl$_3$): δ 5.27 (s, 1H), 5.12 (br. s, 1H), 5.03 (m, 1H), 3.42 (m, 4H), 2.00 (dq, 1H, J=13.9 Hz, J=7.4 Hz), 1.91 (dq, 1H, J=14.0, Hz, J=6.9 Hz), 1.71 (s, 3H), 1.16 (t, 3H, J=6.9 Hz), 1.12 (t, 3H, J=6.9 Hz), 0.88 (t, 3H, J=7.4 Hz) ppm;

$^{13}$C NMR (100 MHz, CDCl$_3$): δ 172.3, 146.9, 111.5, 77.5, 41.4, 41.1, 28.2, 18.9, 13.1, 12.2, 7.8 ppm.

Example 16

Synthesis of (S)-2-N,N-triethyl-2-hydroxy-3-oxo-butyramide (22)

Through a stirred solution of 595.0 mg of compound (21) as obtained from example 15 (2.985 mmol) in 29.8 mL dichloromethane at −78° C., ozone was bubbled (150 L/h) until a blue colour appeared. Subsequently, argon was bubbled through the solution for 20 min. 2.21 mL dimethylsulfide (200.7 mmol, 10.0 eq) were subsequently added and the solution was allowed to slowly warm up to room temperature overnight. The mixture was washed three times with 20 mL water. The organic phase was dried over 5 g sodium sulfate and filtered. The solid was washed with 10 mL dichloromethane. After evaporation of solvent in a rotary evaporator (24° C./10 mbar), the title compound (587.3 mg, 98% by weight) was obtained as a yellow oil.

$[\alpha]_D^{20}$ (c=g/dL, CHCl$_3$)=+77.1. The other analytical data are in accordance with the racemic form of Example 4.

Example 17

Synthesis of (S)-5-diethylcarbamoyl-5-ethyl-4-methyl-2-oxo-2,5-dihydro-furan-3-carboxylic acid ethyl ester (23)

According to procedure described in Example 5, 587.3 mg of compound (22) as obtained from example 16 (2.918 mmol) and 2.29 mL diethylmalonate (14.59 mmol, 5.0 eq) in 23 mL ethanol were treated with 3.822 g cesium carbonate (11.67 mmol, 4.0 eq) yielding the crude product (1.224 g, 141% by weight) as a yellow liquid (er=94.15:5.85).

$[\alpha]_D^{20}$ (c=1.025 g/dL, CHCl$_3$)=−134.8. The other analytical data are in accordance with the racemic form of Example 5.

Example 18

Synthesis of (S)-5-diethylcarbamoyl-4-((E)-2-dimethylamino-vinyl)-5-ethyl-2-oxo-2,5-dihydro-furan-3-carboxylic acid ethyl ester (24)

According to the procedure described in Example 6 1.22 0 g of compound (23) as obtained from example 17 (4.103 mmol) in 7.3 mL dimethyl formamide were treated with 7.55 mL tris(dimethylamino)methane (42.26 mmol, 10.3 eq) yielding the crude product as an orange oil (1.463 mg, 101% by weight).

$[\alpha]_D^{20}$ (c=1.020 g/dL, CHCl$_3$)=−238.9. The other analytical data are in accordance with the racemic form of Example 6.

Example 19

Synthesis of (S)-1-ethyl-3,4-dioxo-13,4,5-tetrahydro-furo[3.4-c]pyridine-1-carboxylic acid diethylamide (25)

According to the procedure as described in Example 8 1.462 g of compound (24) as obtained from example 18 (4.148 mmol) in 11.7 mL dimethyl formamide were treated with 3.263 g ammonium acetate (41.48 mmol, 10.0 eq) yielding the crude product as a red liquid (3.175 g, 275% by weight). All volatile components were removed in a Kugelrohr distillation apparatus (50° C., 0.05 mbar). The residue (402.8 mg, 35% by weight) was purified by trituration for 18 h at room temperature with 4.8 mL methyl tert-butyl ether furnishing the title compound (329.2 mg, 1.18 mmol, 29% by weight, er=93.26:6.74) as yellow crystals.
mp: 199° C.
$[\alpha]_D^{20}$ (c=0.364 g/dL, CHCl$_3$)=−67.9.

The other analytical data are in accordance with the racemic form of Example 8.

Example 20

Synthesis of (S)—N,N-diethyl-2-hydroxy-2-(3-hydroxymethyl-2-oxo-1,2-dihydro-pyridin-4-yl)-butyramide (26)

According to the procedure described in Example 9, 694.0 mg of compound (25) as obtained from example 19 (2.494 mmol) in 28 mL ethanol were treated with 1.537 g cerium (III) chloride (grinded, 6.235 mmol, 2.5 eq) and 1.081 g sodium borohydride (27.4 mmol, 11 eq) yielding the crude product as a beige solid (576.0 mg, 82% by weight), which was redissolved in 10 mL methanol at 60° C. The solution was poured on 88 mL saturated aqueous sodium hydrogencarbonate/brine (1:1) and the resulting suspension was stirred for additional 24 h prior to extraction with five times 88 mL dichloromethane/ethanol mixture (4:1). The combined organic extracts were evaporated in a rotary evaporator (50° C., 5 mbar) yielding the title compound (461.5 mg, 1.63 mmol, 66% by weight) as an off-white solid.
mp: 174° C. (decomposition).
$[\alpha]_D^{20}$ (c=0.253 g/dL, CHCl$_3$)=−81.8.

The other analytical data are in accordance with the racemic form of Example 9.

Example 21

Synthesis of (S)-4-ethyl-4-hydroxy-1,7-dihydro-4H-pyrano[3,4-c]pyridine-3,8-dione (27)

According to the procedure described in Example 10, 461.0 mg of compound (26) as obtained from example 20 (1.633 mmol) in 9.2 mL dimethoxyethane were treated with 1.38 mL concentrated aqueous hydrochloric acid (36.5%, 16.33 mmol, 10.0 eq) yielding the crude product as a lightly yellow solid (722.8 mg, 212% by weight), which was stirred with 2.2 mL methanol at room temperature overnight. The mixture was filtered and the title compound was washed with additional 2.2 mL methanol furnishing the purified product as white crystals (117.4 mg, 34% by weight, er=95.0:5.0 by chiral HPLC).
mp: 226° C. (decomposition);
$[\alpha]_D^{20}$ (c=0.168 g/dL, MeOH)=+102.6 (for a sample with er=98.1:1.9).

The other analytical data are in accordance with the racemic form of Example 10. Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A process for the manufacture of the compound of formula (1):

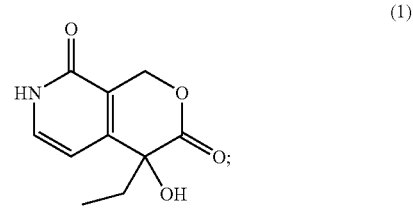

comprising:

a) reacting a compound of formula (I):

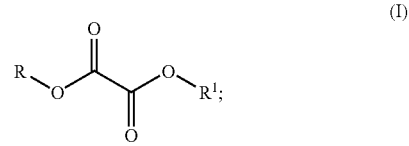

with an amine of formula HNR$^2$R$^3$ to obtain a compound of formula (II):

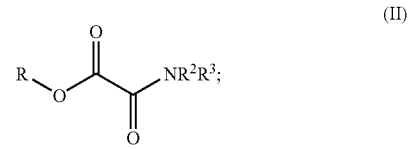

b) further reacting a compound of formula (II) with an ethyl-base to obtain a compound of formula (III):

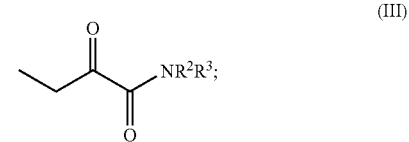

c) further reacting said compound of formula (III) with a compound of formula (IV):

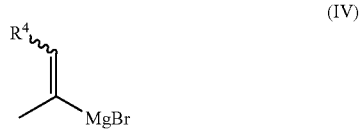

to obtain a compound of formula (V):

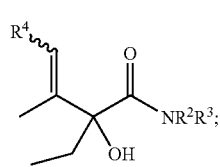

(V)

d) further reacting said compound of formula (V) with ozone to obtain a compound of formula (VI):

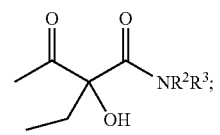

(VI)

e) further reacting said compound of formula (VI) with a compound of formula (VII):

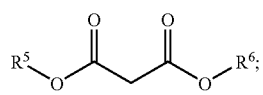

(VII)

and a base, to obtain a compound of formula (VIII):

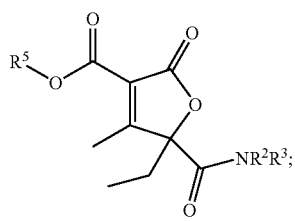

(VIII)

f) further reacting said compound of formula (VIII) with di($C_1$-$C_6$)-alkylformamide, di($C_1$-$C_6$)-alkylacetal or a compound of the formula ($R^7R^8N$)$_3$—CH to obtain a compound of formula (IX):

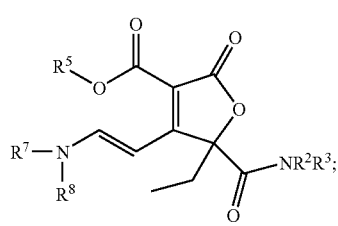

(IX)

g) further reacting said compound of formula (IX) with ammonium acetate to obtain a compound of formula (X):

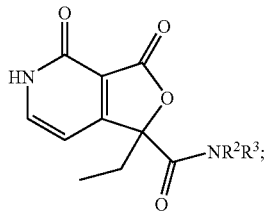

(X)

h) further reacting said compound of formula (X) with alkali metal borohydrides and earth metal salts to obtain a compound of formula (XI):

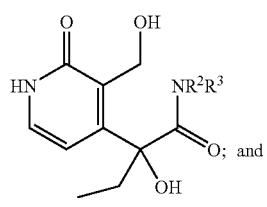

(XI)

i) further reacting said compound of formula (XI) with concentrated mineral acids to obtain the compound of formula (1);

wherein:

R, $R^1$, $R^7$ and $R^8$ independently from each other are ($C_1$-$C_6$)-alkyl;

$R^2$, $R^3$ and $R^4$ independently from each other are selected from the group consisting of ($C_1$-$C_6$)-alkyl and ($C_3$-$C_7$)-cycloalkyl; and $R^5$ and $R^6$ independently from each other are selected from the group consisting of ($C_1$-$C_6$)-alkyl and an aryl group.

2. The process according to claim 1, for the manufacture of the compound of formula (1a):

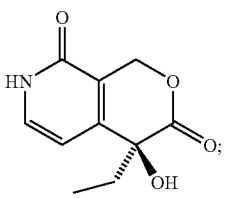

(1a)

comprising:

aa) reacting the compound of formula (2):

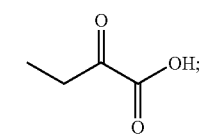

(2)

with a chiral secondary alcohol of the formula R⁹OH to obtain an ester of formula (IIIa):

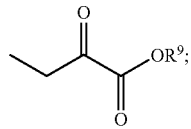
(IIIa)

bb) further reacting said ester of formula (IIIa) with a compound of formula (IVa):

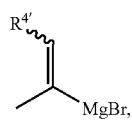
(IVa)

to obtain a compound of formula (Va):

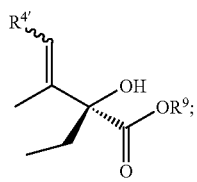
(Va)

cc) chemically cleaving the ester from a compound of formula (Va) carried out in the presence of an alkali metal- or earth alkali metal hydroxide and optionally in the presence of hydrogen peroxide, to obtain the compound of formula (Vb):

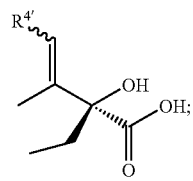
(Vb)

dd) further reacting said compound of formula (Vb) with a tertiary amine and thionyl chloride, then subsequently adding an amine of formula HNR²'R³' to obtain a compound of formula (Vc):

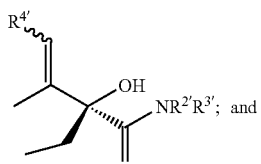
(Vc)

then performing the reaction steps d) to i) according to claim 1, to obtain the compound of formula (1a);

wherein:
R²' has the meaning of R² according to claim 1;
R³' has the meaning of R³ according to claim 1;
R⁴' has the meaning of R⁴ according to claim 1;
—OR⁹ is selected from the group consisting of:

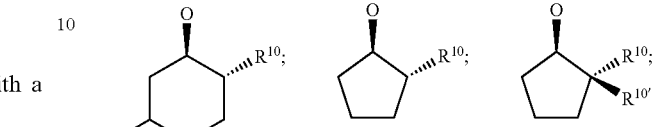

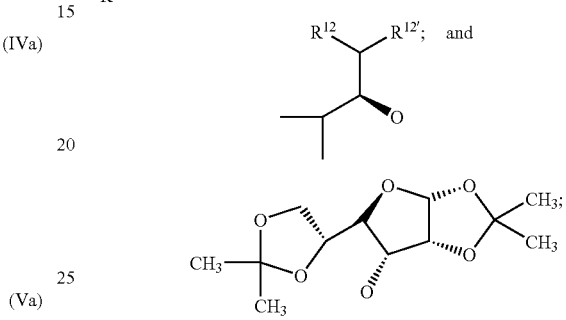

R¹⁰ and R¹⁰' independently from each other are selected from the group consisting of:
(1) an aryl group, which is unsubstituted or substituted by phenyl; and
(2) a (C₃-C₁₂)alkyl group, which is unsubstituted or substituted by phenyl;
R¹¹ is selected from the group consisting of hydrogen and (C₁-C₆)alkyl; and
R¹² and R¹²' independently from each other represent an aryl group.

3. The process according to claim 2, wherein —OR⁹ is selected from the group consisting of:

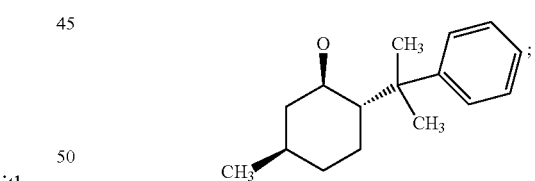

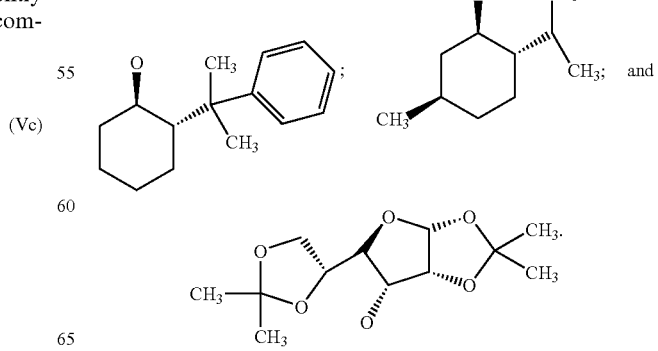

4. The process according to claim 2, wherein —OR$^9$ is selected from the group consisting of:

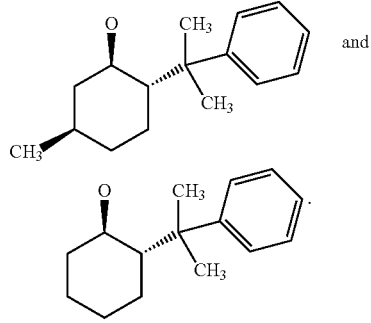

and

5. The process according to claim 1, for the manufacture of the compound of formula (1b):

(1b)

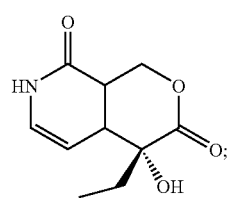

comprising:
aaa) reacting the compound of formula (2):

(2)

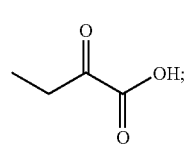

with a chiral secondary alcohol of the formula R$^{18}$OH to obtain an ester of formula (IIIb):

(IIIb)

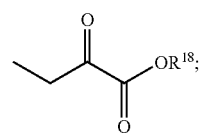

bbb) further reacting said ester of formula (IIIb) with a compound of formula (IVa) according to claim 2:

(IVa)

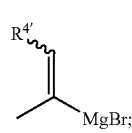

to obtain a compound of formula (Vd):

(Vd)

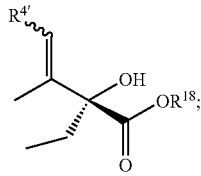

ccc) chemically cleaving the ester from the compound of formula (Vd) in the presence of an alkali metal- or earth alkali metal hydroxide and optionally in the presence of hydrogen peroxide, to obtain the compound of formula (Ve):

(Ve)

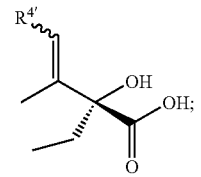

ddd) further reacting said compound of formula (Ve) with a tertiary amine and thionyl chloride, then subsequently adding an amine of formula HNR$^{2'}$R$^{3'}$ according to claim 2 to obtain a compound of formula (Vf):

(Vf)

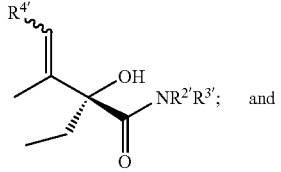

and then performing the reaction steps d) to i) according to claim 1, to obtain the compound of formula (1b);
wherein:
R$^{2'}$ has the meaning according to claim 2;
R$^{3'}$ has the meaning according to claim 2;
R$^{4'}$ has the meaning according to claim 2;
—OR$^{18}$ is selected from the group consisting of:

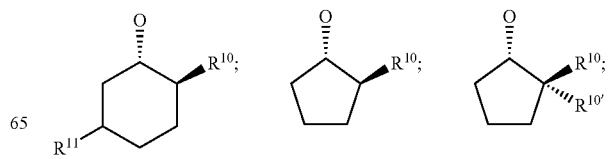

-continued

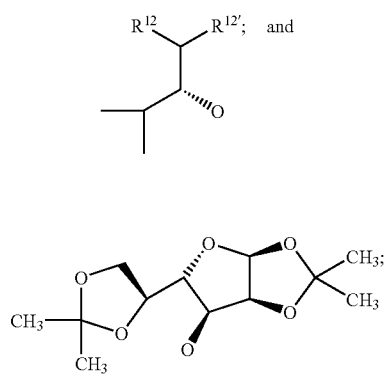

$R^{10}$ and $R^{10'}$ independently from each other are selected from the group consisting of:
  (1) an aryl group, which is unsubstituted or substituted by phenyl; and
  (2) a $(C_3\text{-}C_{12})$alkyl group, which is unsubstituted or substituted by phenyl;
$R^{11}$ is selected from the group consisting of hydrogen and $(C_1\text{-}C_6)$alkyl; and
$R^{12}$ and $R^{12'}$ independently from each other represent an aryl group.

6. The process according to claim 1, wherein:
R, $R^1$, $R^2$, $R^3$, $R^5$ and $R^6$ are ethyl; and
$R^4$, $R^7$ and $R^8$ are methyl.

7. The process according to claim 2, wherein:
$R^{2'}$ and $R^{3'}$ are ethyl;
$R^{4'}$ is methyl; and
—$OR^9$ is

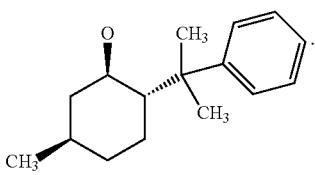

8. The process according to claim 2, wherein said compound of formula (1a) is transformed into a compound of formula (A):

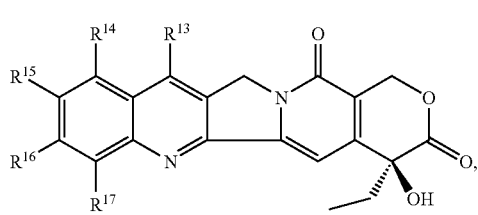

(A)

comprising the steps of:
  a) further reacting said compound of formula (1a) with a compound of formula (B):

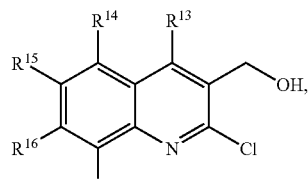

(B)

with diisopropyl azodicarboxylate, ethyldiphenylphosphine and dimethylacetamide, to obtain a compound of formula (C):

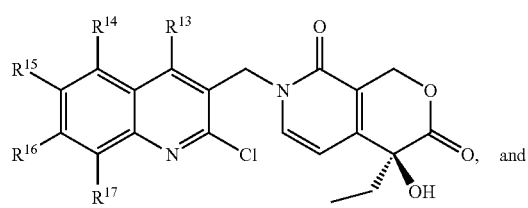

(C)

b) further reacting said compound of formula (C) with palladium (II) acetate, potassium acetate, triphenylphosphine, tetrabutyl ammonium bromide and acetonitrile to obtain the corresponding compound of formula (A);
wherein:
$R^{13}$ and $R^{14}$ are independently selected from the group consisting of hydrogen; halogen; cyano; $(C_1\text{-}C_6)$alkyl; —O—$(C_1\text{-}C_6)$alkyl; —S—$(C_1\text{-}C_6)$alkyl; hydroxyl; amino; mono $(C_1\text{-}C_6)$alkyl amino; di$(C_1\text{-}C_6)$alkyl amino; nitro; and trifluoromethyl; or alternatively, $R^{13}$ and $R^{14}$ together with the carbon atoms to which they are attached form a six-membered, unsaturated cyclic hydrocarbon, wherein one or two carbon atoms are optionally replaced with nitrogen and which is unsubstituted or once substituted by a $(C_1\text{-}C_6)$alkyl;
$R^{15}$, $R^{16}$ and $R^{17}$ are independently selected from the group consisting of hydrogen; halogen; cyano; $(C_1\text{-}C_6)$alkyl; —O—$(C_1\text{-}C_6)$alkyl; —S—$(C_1\text{-}C_6)$alkyl; hydroxyl; amino; mono $(C_1\text{-}C_6)$alkyl amino; di$(C_1\text{-}C_6)$alkyl amino; nitro; and trifluoromethyl.

9. The process according to claim 1, wherein the compound of formula (1) is transformed into a compound of formula (A-1):

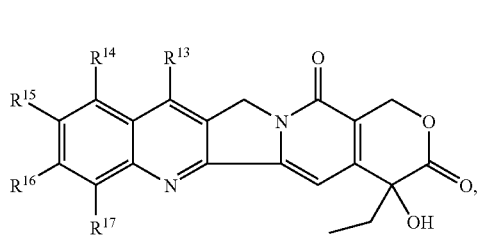

comprising the steps of:
a) further reacting said compound of formula (1) with a compound of formula (B) according to claim 8:

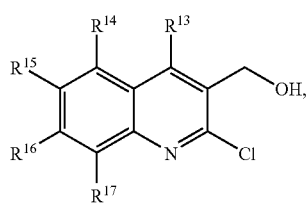

in the presence of diisopropyl azodicarboxylate, ethyldiphenylphosphine and dimethylacetamide, to obtain a compound of formula (C-1):

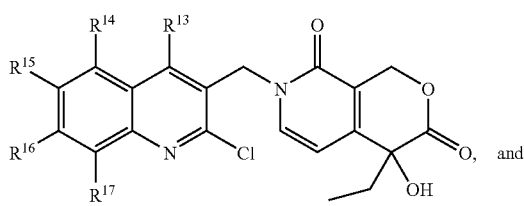

b) further reacting said compound of formula (C-1) with palladium (II) acetate, potassium acetate, triphenylphosphine, tetrabutyl ammonium bromide and acetonitrile to obtain the corresponding compound of formula (A-1), wherein $R^{13}$, $R^{14}$, $R^{15}$, $R^{16}$ and $R^{17}$ are defined according to claim 8.

10. The process according to claim 5, wherein said compound of formula (1b) is transformed into a compound of formula (A-2):

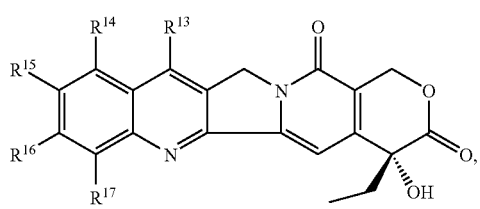

comprising the steps of:
a) further reacting said compound of formula (1b) with a compound of formula (B) according to claim 8:

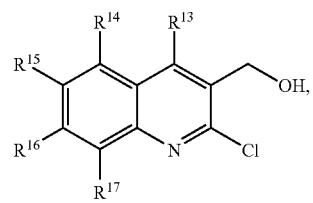

in the presence of diisopropyl azodicarboxylate, ethyldiphenylphosphine and dimethylacetamide, to obtain a compound of formula (C-2):

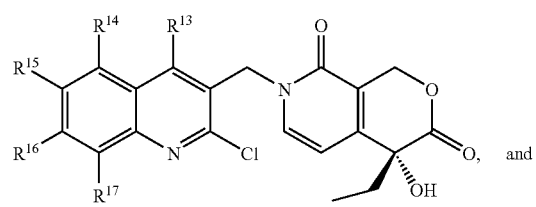

b) further reacting said compound of formula (C-2) with palladium (II) acetate, potassium acetate, triphenylphosphine, tetrabutyl ammonium bromide and acetonitrile to obtain the corresponding compound of formula (A-2), wherein:
$R^{13}$, $R^{14}$, $R^{15}$, $R^{16}$ and $R^{17}$ are defined according to claim 8.

11. The process according to claim 8, wherein $R^{13}$ and $R^{14}$ together with the carbon atoms to which they are attached form a 1-pentyl-pyrimidine moiety and $R^{15}$, $R^{16}$ and $R^{17}$ are all hydrogen, to give the compound of formula (3a):

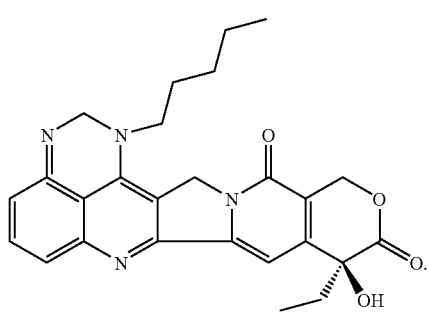

12. The process according to claim 8, wherein $R^{13}$, $R^{14}$, $R^{15}$, $R^{16}$ and $R^{17}$ are all hydrogen, to give the compound of formula (3):

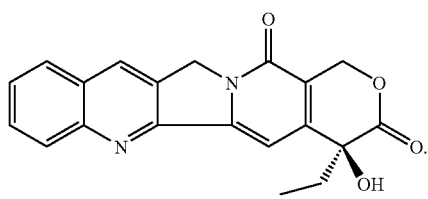

* * * * *